United States Patent
Jimenez et al.

(10) Patent No.: US 8,703,731 B2
(45) Date of Patent: Apr. 22, 2014

(54) SPHINGOSINE-BOUND SIRNA

(75) Inventors: Ana Isabel Jimenez, Madrid (ES); Gema Panizo, Madrid (ES); Tamara Martinez, Madrid (ES); Anna Avino, Barcelona (ES); Clara Caminal, Barcelona (ES); Ramon Eritja, Barcelona (ES); Santiago Grijalvo, Barcelona (ES)

(73) Assignee: Sylentis S.A.U., Madrid (ES)

( * ) Notice: Subject to any disclaimer, the term of this patent is extended or adjusted under 35 U.S.C. 154(b) by 0 days.

(21) Appl. No.: 13/379,241

(22) PCT Filed: Jun. 22, 2010

(86) PCT No.: PCT/GB2010/051025
§ 371 (c)(1),
(2), (4) Date: Feb. 16, 2012

(87) PCT Pub. No.: WO2010/150004
PCT Pub. Date: Dec. 29, 2010

(65) Prior Publication Data
US 2012/0142765 A1 Jun. 7, 2012

(30) Foreign Application Priority Data
Jun. 22, 2009 (GB) .................................. 0910723.6

(51) Int. Cl.
C12N 15/11 (2006.01)
C07H 21/04 (2006.01)

(52) U.S. Cl.
USPC ........................................ 514/44 A; 536/24.5

(58) Field of Classification Search
USPC ........................................ 536/24.5; 514/44 A
See application file for complete search history.

(56) References Cited

U.S. PATENT DOCUMENTS

| 5,149,860 A * | 9/1992 | Zysman et al. ................ 560/160 |
| 2005/0025820 A1 * | 2/2005 | Kester et al. .................. 424/450 |
| 2005/0026278 A1 * | 2/2005 | Tuschl et al. .................. 435/375 |
| 2006/0234909 A1 * | 10/2006 | Newman et al. .................. 514/2 |

FOREIGN PATENT DOCUMENTS

| WO | WO 2004/065601 A2 | 8/2004 |
| WO | WO 2006/073458 A2 | 7/2006 |
| WO | WO 2008/014979 A2 | 2/2008 |
| WO | WO 2008/109105 A2 | 9/2008 |
| WO | WO 2008/139262 A2 | 11/2008 |
| WO | WO 2009/009025 A1 | 1/2009 |
| WO | WO 2009/054551 A2 | 4/2009 |

OTHER PUBLICATIONS

Lorenz et al., "Steroid and Lipid Conjugates of siRNAs to Enhance Cellular Uptake and Gene Silencing in Liver Cells," Bioorganic & Medicinal Chemistry Letters, vol. 14, pp. 4975-4977, 2004.

Manoharan, "Oligonucleotide Conjugates as Potential Antisense Drugs with Improved Uptake, Biodistribution, Targeted Delivery and Mechanism of Action," Antisense & Nucleic Acid Drug Development, vol. 12, pp. 103-128, 2002.

Ueno et al, "Synthesis and Silencing Properties of siRNAs Possessing Lipophilic Groups at their 3'-termini," Bioorganic & Medicinal Chemistry, vol. 16, pp. 7698-7704, 2008.

Wolfrum et al, "Mechanisms and optimization of in vivo delivery of lipophilic siRNAs," Nature Biotechnology, vol. 25, No. 10, pp. 1149-1157, Oct. 2007.

* cited by examiner

Primary Examiner — Brian Whiteman
(74) Attorney, Agent, or Firm — Margaret B. Brivanlou; King & Spalding LLP

(57) ABSTRACT

The invention relates to novel oligomer analogues and their use in oligonucleotide-based therapies. More specifically, the invention concerns oligonucleotides carrying lipid molecules and their use as potential inhibitors of gene expression.

30 Claims, 10 Drawing Sheets

| Entry | structure |
|---|---|
| 1 | $T_8 - O^{5'}PO_3-(CH_2)_6-NH\overset{O}{\overset{\|}{C}}NH-\underset{H}{\overset{CH_2OH}{\underset{\|}{C}}}-\underset{OH}{\overset{H}{\underset{\|}{C}}}-\overset{H}{\underset{\|}{C}}=\overset{}{\underset{H}{C}}-C_{13}H_{27}$ |
| 2 | $T_8 - O^{5'}PO_3(CH_2)_9\overset{O}{\overset{\|}{C}}NH-\underset{H}{\overset{CH_2OH}{\underset{\|}{C}}}-\underset{OH}{\overset{H}{\underset{\|}{C}}}-\overset{H}{\underset{\|}{C}}=\underset{H}{C}-C_{13}H_{27}$ |
| 3 | $T_8-O^{3'}PO_3-(CH_2)_3\overset{O}{\overset{\|}{C}}\underset{HO(H_2C)_6HNOC}{\underset{\|}{NH}}(CH_2)_4-\underset{H}{\overset{}{N}}\overset{O}{\overset{\|}{C}}\underset{H}{\overset{}{N}}-\overset{CH_2OH}{\underset{OH}{\overset{H}{\underset{\|}{C}H}}}\overset{H}{\underset{\|}{C}}=\underset{H}{C}-C_{13}H_{27}$ |
| 4 | $HO-\overset{-NHCO\frown O\frown O^{3'}-OPO_3-T_8}{\underset{-NHCO\frown O\frown OPO_3-(CH_2)_9\underset{\|}{\overset{H}{N}}\overset{}{\underset{O}{\overset{\|}{C}}}\underset{H}{\overset{CH_2OH}{\underset{OH}{C}}}\overset{H}{\underset{\|}{C}}=\underset{H}{C}-C_{13}H_{27}}{}$ |
| 5 | $T_8-O^{3'}PO_3(CH_2)_3\overset{O}{\overset{\|}{C}}\underset{HO(H_2C)_6HNOC}{\underset{\|}{NH}}(CH_2)_2\overset{}{\underset{O}{\overset{\|}{C}}}\underset{H}{\overset{}{N}}-\overset{CH_2OH}{\underset{OH}{\overset{H}{\underset{\|}{C}H}}}\overset{H}{\underset{\|}{C}}=\underset{H}{C}-C_{13}H_{27}$ |

Figure 5

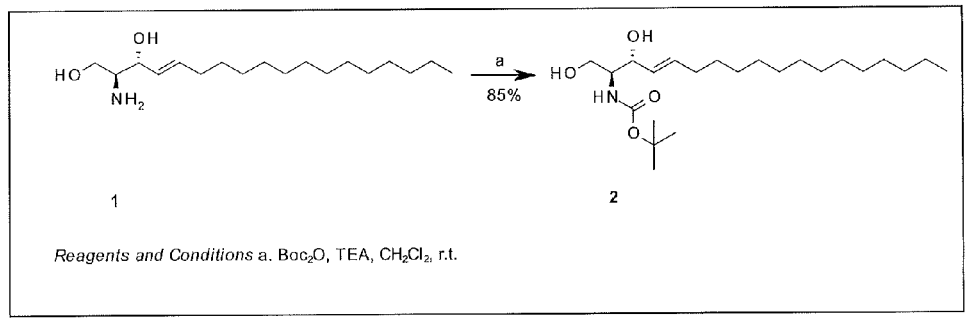
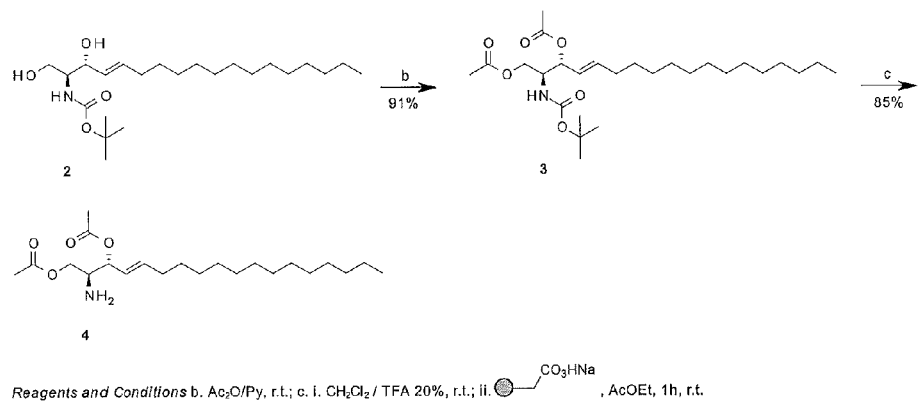
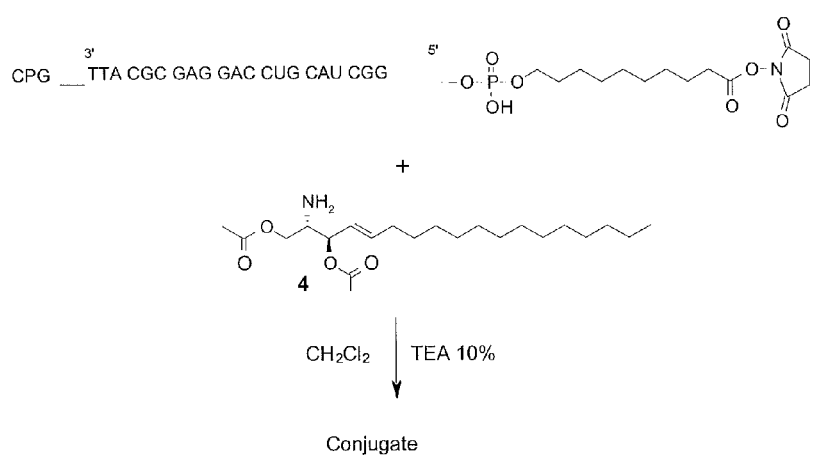
Figure 7

SPHINGOSINE-BOUND SIRNA

FIELD OF THE INVENTION

The invention relates to novel oligomer analogues and their use in oligonucleotide-based therapies. More specifically, the invention concerns oligonucleotides carrying lipid molecules and their use as potential inhibitors of gene expression.

BACKGROUND OF THE INVENTION

RNA interference (RNAi) is a naturally occurring regulatory mechanism of most eukaryotic cells that uses small double stranded RNA (dsRNA) molecules to direct homology-dependent gene silencing. Its discovery by Fire and Mello in the worm *C. elegans* {Fire, 1998} was awarded the Nobel prize in 2006. Shortly after its first description, RNAi was also shown to occur in mammalian cells, not through long dsRNAs but by means of double-stranded small interfering RNAs (siRNAs) 21 nucleotides long {Elbashir, 2001}.

The process of RNA interference is thought to be an evolutionarily-conserved cellular defence mechanism used to prevent the expression of foreign genes and is commonly shared by diverse flora, where it is called post-transcriptional gene silencing, and phyla. Since the discovery of RNAi mechanism there has been an explosion of research to uncover new compounds that can selectively alter gene expression as a new way to treat human disease by addressing targets that are otherwise "undruggable" with traditional pharmaceutical approaches involving small molecules or proteins.

According to current knowledge, the mechanism of RNAi is initiated when long double stranded RNAs are processed by an RNase III-like protein known as Dicer. The protein Dicer typically contains an N-terminal RNA helicase domain, an RNA-binding so-called Piwi/Argonaute/Zwille (PAZ) domain, two RNase III domains and a double-stranded RNA binding domain (dsRBD) {Collins, 2005} and its activity leads to the processing of the long double stranded RNAs into 21-24 nucleotide double stranded siRNAs with 2 base 3' overhangs and a 5' phosphate and 3' hydroxyl group. The resulting siRNA duplexes are then incorporated into the effector complex known as RNA-induced silencing complex (RISC), where the antisense or guide strand of the siRNA guides RISC to recognize and cleave target mRNA sequences {Elbashir, 2001} upon adenosine-triphosphate (ATP)-dependent unwinding of the double-stranded siRNA molecule through an RNA helicase activity {Nykanen, 2001}. The catalytic activity of RISC, which leads to mRNA degradation, is mediated by the endonuclease Argonaute 2 (AGO2) {Liu, 2004; Song, 2004}. AGO2 belongs to the highly conserved Argonaute family of proteins. Argonaute proteins are ~100 KDa highly basic proteins that contain two common domains, namely PIWI and PAZ domains {Cerutti, 2000}. The PIWI domain is crucial for the interaction with Dicer and contains the nuclease activity responsible for the cleavage of mRNAs {Song, 2004}. AGO2 uses one strand of the siRNA duplex as a guide to find messenger RNAs containing complementary sequences and cleaves the phosphodiester backbone between bases 10 and 11 relative to the guide strand's 5' end {Elbashir, 2001}. An important step during the activation of RISC is the cleavage of the sense or passenger strand by AGO2, removing this strand from the complex {Rand, 2005}. Crystallography studies analyzing the interaction between the siRNA guide strand and the PIWI domain reveal that it is only nucleotides 2 to 8 that constitute a "seed sequence" that directs target mRNA recognition by RISC {Ma, 2005}. Once the mRNA has been cleaved, and due to the presence of unprotected RNA ends in the fragments, the mRNA is further cleaved and degraded by intracellular nucleases and will no longer be translated into proteins {Orban, 2005} while RISC will be recycled for subsequent rounds {Hutvagner, 2002}. This constitutes a catalytic process leading to the selective reduction of specific mRNA molecules and the corresponding proteins. It is possible to exploit this native mechanism for gene silencing with the purpose of regulating any gene(s) of choice by directly delivering siRNAs effectors into the cells or tissues, where they will activate RISC and produce a potent and specific silencing of the targeted mRNA.

Many studies have been published describing the ideal features a siRNA should have to achieve maximum effectiveness, regarding length, structure, chemical composition, and sequence. Initial parameters for siRNA design were set out by Tuschl and co-workers in WO02/44321, although many subsequent studies and/or improvements have been published since then.

Also, a lot of effort has been put into enhancing siRNA stability as this is perceived as one of the main obstacles for therapy based on siRNA, given the ubiquitous nature of RNAses. One of the main strategies followed for stability enhancement has been the use of modified nucleotides such as 2'-O-methyl nucleotides, 2'-amino nucleotides, nucleotides containing 2'-O or 4'-C methylene bridges. Also, the modification of the ribonucleotide backbone connecting adjacent nucleotides has been described, mainly by the introduction of phosphorothioate modified nucleotides. It seems that enhanced stability is often inversely proportional to efficacy (Parish, 2000), and only a certain number, positions and/or combinations of modified nucleotides may result in a stable silencing compound. As this is an important hurdle within siRNA-based treatments, different studies have been published which describe certain modification patterns which show good results, examples of such are for example EP1527176, WO2008/050329, WO2008/104978 or WO2009/044392, although many more may be found in the literature.

Another strategy to achieve efficient siRNA delivery to target cells has been the use of lipids, which can envelope the siRNA compound, thus making it inaccessible to nucleases. As such, strategies based on siRNA packaging into liposomes have been described. Further sophisticated solutions along these lines are small nucleic acid lipid particles or SNALPs, which are described for example in patent applications US2006134189, US2006240093 or US2007135372. The lipids used may be cationic lipids, non-cationic lipids and conjugated lipids, even lipids containing polyalkylamine chains as a capturing agent of nucleic acid molecules have been used (WO2004/110499). Another alternative are the lipoplex formulations described in WO2007/121947, based on a liposome containing a helper lipid and a shielding compound which is bound to the nucleic acid, in which said shielding compound-nucleic acid complex is liberated from the lipid composition under in vivo conditions. In a specific embodiment the lipoplex formulation comprises a siRNA and a shielding compound which is a conjugate of PEG and ceramide.

The conjugation of lipid molecules to oligonucleotides such as cholesterol (Boutorine, 1993; Gryaznov, 1993; Zelphati, 1994) is shown to produce oligonucleotide conjugates with improved inhibitory properties (Godard, 1995; Le Doan, 1999; Soutscheck, 2004; Wolfrum, 2007). Efficient and selective uptake of these siRNA conjugates depends on interactions with lipoprotein particles, lipoprotein receptors and transmembrane proteins. High-density lipoprotein directs siRNA delivery into liver, gut, kidney and steroidogenic organs, whereas low-density lipoprotein targets siRNA primarily to the liver. As such different lipid conjugates will probably enhance delivery to different organs, thereby allowing treatment of different diseases.

In the present invention we describe the preparation and properties of oligonucleotides conjugated to sphingolipids.

DESCRIPTION OF THE DRAWINGS

FIG. 5 contains a table showing the structure of the octathymidyl derivatives carrying sphingosine prepared by postsynthetic conjugation.

FIG. 7 shows a schematic representation of the synthesis of oligonucleotide 5'-sphingosine conjugates.

DETAILED DESCRIPTION OF THE INVENTION

Figure 1:
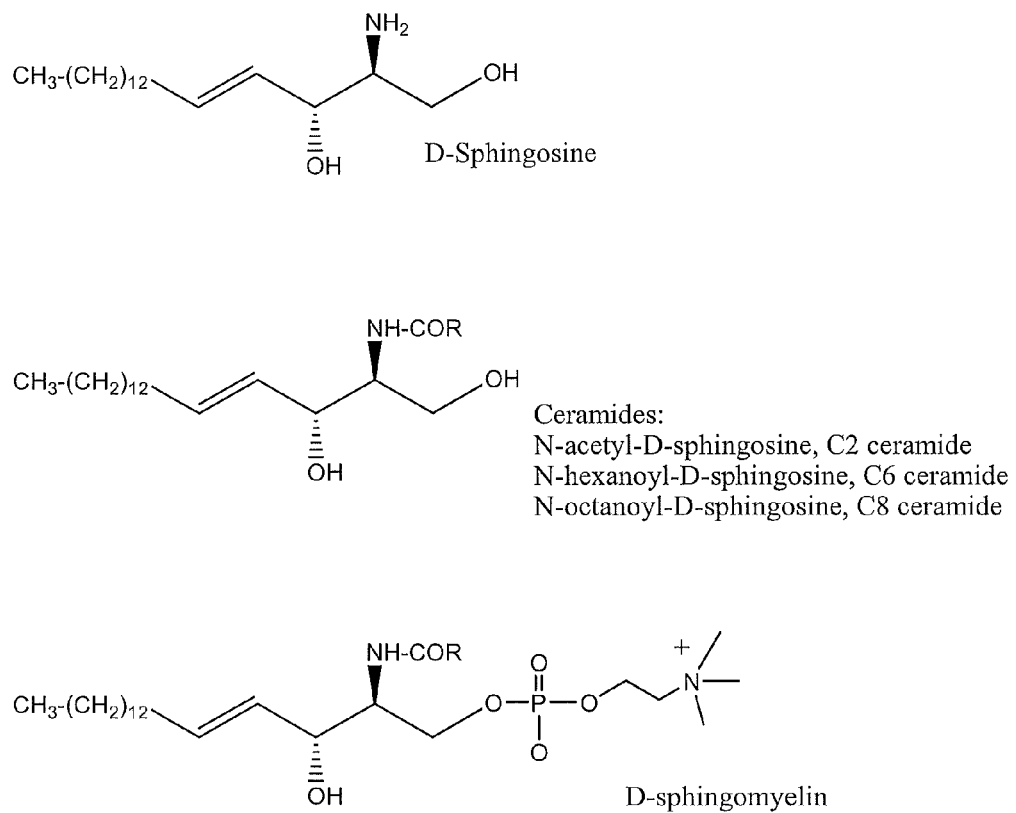
FIG. 1 shows a schematic representation of different sphingolipid molecules within the meaning of the present invention. (a) D-sphingosine, (b) D-ceramide, (c) D-sphingomyelin.

Sphingolipids are complex lipids derived from the unsaturated 18 carbon organic aliphatic amino alcohol sphingosine; sphingosine is bound to a long-chained fatty acid by an amide bond, forming a ceramide. They are an important class of lipids in animal and plant cell membranes and are the most abundant lipids within the tissues of more complex organisms.

All sphingolipids have three basic components: the main component is a long chain amino alcohol named sphingosine (1,3-dihydroxy-2-amino-4-octadecene). Carbons 1, 2 and 3 of this molecule are functional group carriers (—OH, $NH_2$, —OH) and when a saturated or unsaturated long chain fatty acid binds carbon 2 via an amide bond, the result is a ceramide, which is the fundamental structural unit of all sphingolipids. This type of lipid may be found in especially large quantities in nerve and brain tissue. Sphingosine, with its free amino group, isn't found in nature.

Sphingolipids are divided into 3 subclasses, ceramides, sphingomyelins, and glycosphingolipids.

Ceramides are the simplest sphingolipids, and are widely distributed in plant and animal tissues. The other sphingolipids are derivatives of ceramides.

Sphingomyelins contain a phosphate group, bound to hydroxyl group 1 on the ceramide, which is esterified with choline (phosphocholine) or ethanolamine (phosphoethanolamine) to form the polar group or "head" of the molecule. It is the only phosphorus containing sphingolipid and may, as such, be considered a phospholipid, but is usually classified as a sphingolipid due to its structural components. Sphingomyelins are present in animal plasma membranes, in the myelin sheath which covers and isolates the axons of myelinated neurons. Sphingomyelin is one of the main structural lipids within nervous tissue membranes.

Glycosphingolipids or simply glycolipids are formed by the hydroxyl group 1 of the ceramide binding, via a glycosidic bond, to a monosaccharide or an oligosaccharide, which normally project outwards towards the outer face of the plasma membrane. Most frequent monosaccharides are D-glucose, D-galactose and N-acetylgalactosamine. Various types are known:

Cerebrosides. Cerebrosides have a single sugar bound via a β-glycosidic bond to the ceramide's hydroxyl group; those which contain galactose (galactocerebrosides), are found characteristically in plasma membranes of nervous tissue cells, whereas those which contain glucose (glucocerebrosides) are found in the plasma membranes of cells from non-nervous tissues. Sulphatides contain a galactose esterified with sulphate at carbon 3, and occur in the white matter of the brain.

Globosides. Globosides or ceramide oligosaccharides are glycosphingolipids with neutral oligosaccharides bound to the ceramide.

Gangliosides. These are the most complex sphingolipids due to big polar heads formed by units of negatively charged oligosaccharides, which have their origin in the existence of one or more units of N-acetylneuraminic or syalic acid, which has a negative charge at pH 7. Gangliosides differ from cerebrosides in that they contain this acid group. They are concentrated in high quantities in ganglion cells of the central nervous system, especially at nerve ends. Gangliosides constitute 6% of lipid membranes of the grey matter of the human brain and may be found in smaller quantities in the membranes of most non-nervous animal tissues. They may be found in the external zone of the membrane and serve in cell recognition, and are thus considered membrane receptors.

Sphingolipid molecules present amphipathic properties, i.e. both hydrophobic and hydrophilic, which allow them to play an important role in biological membrane formation. Some glycosphingolipids are found on the surface of erythrocytes and other cells, behaving as antigens and defining blood types.

Sphingolipids are of biological importance due to their role in cell signalling. For example, ceramide is widely recognised as a cell apoptosis inductor. If ceramide is degraded by ceramidases, sphingosine is liberated, which if it is in turn phosphorylated, results in sphingosine 1-phosphate, that has a completely antagonistic effect to ceramide by inducing cell proliferation and mitosis. Consequently, the balance between ceramide and sphingosine-1-phosphate is very important for the control of cell death and survival.

Given the fact that sphingolipids are a natural component of cell membranes, we have hypothesized that conjugating them to RNA interfering structures, would enhance cell uptake of the gene silencing compounds and may also serve as protective groups against RNAses. As such, the present invention encompasses both these novel structures and their synthesis.

A first aspect of the present invention relates to RNA interfering structures conjugated to different kinds of sphingolipid as defined above, including but not limited to sphingosine, ceramides, sphingomyelin derivatives, cerebrosides and gangliosides. Consequently, within the context of the present invention sphingolipids are also considered to encompass sphingosine.

The term sphingosine also encompasses sphingosine molecules which contain one or more of the following modifications: N-acyl derivatives, N-sulfonamides, hydrogenated double bond, shorter aliphatic chains, heteroatoms forming part of the aliphatic chain, O-alkylated derivatives, addition of hydroxyl groups in the aliphatic chain, and/or addition of alkyl groups in the aliphatic chain.

This is the first time that oligonucleotide containing sphingolipids have been synthesised. Consequently, a further aspect of the present invention is the process of preparation of these oligonucleotides characterised in that it comprises the conjugation of an oligonucleotide to a sphingolipid. Preferred embodiments of the present invention include oligonucleotide conjugation to sphingosine, ceramides, sphingomyelins or glycosphingolipids such as cerebrosides and gangliosides. A particularly preferred embodiment of the present application is the process of oligonucleotide conjugation to D-sphingosine.

Within the meaning of the present invention an oligonucleotide is a nucleic acid polymer, typically containing up to 200 bases. These bases may be either deoxyribonucleic acids or ribonucleic acids, or both.

As is known in the art, each nucleotide contains a sugar (ribose or deoxyribose), with carbons numbered 1' through 5', a nitrogen base and a phosphate group. The base is attached to the 1' position, generally adenine (A), cytosine (C), guanine (G), thymidine (T) or uracil (U). The phosphate group is attached to the 3' position of one sugar and the 5' position of the next, acting as a link between nucleotides. As such, an oligonucleotide chain has two distinct ends, its 5' end, which refers to the free 5' position of the sugar, and at the opposite end of the oligonucleotide, the last sugar will have its 3' position bound to a free phosphate group (as its 5' position will be linked to the previous nucleotide in the chain).

However, the term oligonucleotide within the meaning of the present invention should be understood to include, in some embodiments, alternative bases comprising structural modifications such as those described in the section termed background of the invention, and also alternative bases such as inosine, 4-thiouracil, 5-bromouracil, 5-iodouracil or 3-(aminoallyl)uracil.

For clarity purposes, the term "conjugation" within the present invention is considered to be equivalent to chemical bonding, covalent bonding, chemical coupling or other terms known by an expert in the field. Within the meaning of the present invention, a preferred embodiment of the term conjugation refers to the formation of phosphate or amide bonds.

A further aspect of the present invention is a process for the preparation of sphingolipid containing oligonucleotides characterised in that the conjugation of an oligonucleotide with a sphingolipid comprises:

binding of an amine or carboxy group to at least one terminus of an oligonucleotide, either 5' or 3' or both; and activating said amino or carboxy group; and allowing an amino group on a sphingolipid to attack the activated group on the oligonucleotide, such that the activated group is displaced and a conjugated oligonucleotide-sphingolipid is formed.

A further aspect of the above described process, relates to said process taking place wherein the sphingolipid is provided on a solid support, and the assembly of the oligonucleotide sequence takes place on said solid support.

Another further aspect of this process occurs when said sphingolipid is provided on a solid support, and the assembly of the oligonucleotide sequences takes place from an alcohol function of the sphingosine by successive additions of the nucleoside phosphoramidites or any other DNA synthesis reagent such as nucleoside H-phosphonates, or nucleoside O-phenyl protected phosphodiesters.

In another alternative aspect, the above described process may be performed in such a way that said sphingolipid is reacted with an activated oligonucleotide in solution.

Although a detailed description of the conjugation method is given in the Examples section, the following paragraphs provide a brief description of certain preferred embodiments of the method of synthesis of the present invention.

One method for the synthesis of oligonucleotide conjugates containing sphingosine, comprises the introduction of a carboxylic acid group in the oligonucleotide (either at the 3' or the 5' end) which allows the formation of an amide bond with the amine group on the sphingosine molecule. Amide formation can take place in solution when the oligonucleotide-COOH reacts with the sphingosine molecule or preferably, on a solid phase.

A particularly preferred embodiment, regarding oligonucleotide conjugation to sphingosine (applicable to different types of sphingolipids within the scope of the present invention), is a process comprising the following steps:

protection of the amine group on the sphingosine molecule;
protection of the primary hydroxyl group on the sphingosine molecule;
reaction of the secondary hydroxyl group on the sphingosine with a functionalized support;
oligonucleotide coupling to the sphingosine support, said oligonucleotide having an activated terminus obtained as described in preceding paragraphs,
cleavage of product from the solid support;
isolation of the product, preferably by precipitation; and
purification of the end product, preferably using RP-HPLC (reverse phase, high performance liquid chromatography).

Regarding the synthesis of oligonucleotide conjugates with ceramides, in one preferred embodiment, the method comprises obtaining the corresponding phosphoramidites which are subsequently used to introduce ceramides at the 5' position of the oligonucleotides using oligonucleotide synthesis techniques well known in the art. The first phosphoramidite would yield a phosphate group at position 1, which is the same position as that of the phosphatidyl-choline in sphingomyelin. This phosphoramidite implies introducing a DMT group in the primary alcohol and introducing an orthogonal protecting group in the 2'-OH (usually a silyl derivative), and finally introducing the phosphoramidite function at the 3'-OH.

Another embodiment of the present invention concerns the conjugation of oligonucleotides with sphingomyelin derivatives. Preferred sphingomyelin derivatives are D-sphingosine 1-phosphate, D-ceramidephosphoryl ethanol amine and D-sphingomyelin, although different derivatives known in the art are to be considered within the scope of the present invention. The synthesis of these conjugates preferably comprises reacting the ethanolamine group present in sphingomyelin with oligonucleotides containing carboxylic acid groups, in a manner similar to that described in preceding paragraphs.

Further preferred aspects of the present invention concern the compounds resulting from the above described methods. Consequently, a preferred embodiment of the present invention is a compound characterised in that it comprises an oligonucleotide conjugated to a sphingolipid. Further preferred sphingolipids forming part of this novel compound are selected from among sphingosine, ceramides, sphingomyelins and glycosphingolipids. An especially preferred embodiment being an oligonucleotide conjugated to D-sphingosine.

The compound of the present invention is preferably provided as naked RNA, i.e. without being part of further delivery vehicles of a more complex structure, as for example micelles.

As is described in detail in the Examples of the present specification, it is possible to conjugate a sphingolipid both to the 3' end of the nucleotide and to its 5' end. Consequently, a preferred embodiment of the present invention is a compound comprising an oligonucleotide conjugated to a sphingolipid wherein said sphingolipid is bound to its 3' end, to its 5' end or a sphingolipid is conjugated to each of the 3' and 5' ends of the oligonucleotide, wherein both sphingolipid molecules are the same or different.

The compound of the present invention may also be found hybridised to another oligonucleotide, forming a double-stranded structure. As is known in the art, nucleotide chains may hybridise with one another by complementary base-pairing, i.e. hydrogen bonds established between adenosine and thymidine/uracil or between cytosine and guanine on opposing strands. These double-stranded structures assemble in an antiparallel manner, so that the 5' end of one strand hybridises to the 3' end of the other strand. Thus a further embodiment of this invention comprises the compound of the invention hybridised to another oligonucleotide, preferably this second oligonucleotide will be at least 90% homologous to the sphingolipid-conjugated oligonucleotide. In a further preferred embodiment, both oligonucleotides forming said double-stranded structure are bound to a sphingolipid at one or both of their ends.

In a preferred specific embodiment of the present invention the double-stranded oligonucleotide structure which is bound to a sphingolipid is an RNA interference mediating oligonucleotide, such as for example, a short interfering RNA (siRNA).

As has been described in preceding paragraphs, siRNAs within the meaning of the present invention are double-stranded RNA molecules, with a typical length of between 15 and 25 nucleotides.

Naturally occurring siRNAs usually have between 1 and 3 overhanging nucleotides at their 3' ends, these structures being considered within the scope of the present invention. Moreover, the majority of artificially developed siRNAs have a 19 nucleotide double-stranded structure with 2 overhanging nucleotides at the 3' ends, these latter siRNAs conjugated to sphingolipids either at their 3' or 5' ends or both, are considered a preferred embodiment of the present invention. Similarly, these structures whose overhanging nucleotides consist of deoxyribose bases are also considered preferred embodiments within the meaning of the present invention.

On the other hand, blunt-ended siRNAs have been developed which are very efficient at mediating gene silencing, and these structures may also be conjugated to sphingolipids within the meaning of the present invention. In a preferred embodiment, these blunt-ended siRNAs are between 15 and 25 nucleotides in length, in a more preferred embodiment, between 19 and 23 nucleotides in length. In a particularly preferred embodiment these blunt-ended siRNAs are 19 nucleotides in length and are conjugated to sphingolipids either at the 3' or the 5' end or both.

Irrespective of the siRNA structure, given that these molecules are double-stranded, in a specific embodiment of the present invention the sphingolipid is conjugated to the sense strand, or the antisense strand, or to both strands simultaneously of the given siRNA molecule.

In a particularly preferred embodiment of the present invention, the sphingolipid conjugated to any of the above defined siRNA structures is sphingosine, more preferably D-sphingosine.

Oligonucleotides which regulate gene expression have become of great interest in industry in the latter years. They are used both as research tools, and are therefore supplied by a number of companies, and as potential drugs. The first antisense oligonucleotide-based drug to reach the market is known as Vitravene™, and is administered by intravitreal injection to treat CMV retinitis in AIDS patients. Similarly, the first aptamer (oligonucleotide which binds a target protein thus inhibiting its function) to be approved is Macugen™, also delivered by intravitreal injection to treat wet age-related macular degeneration. Also, the most advanced siRNA drugs in clinical trials are to be administered by intravitreal injection to treat wet age-related macular degeneration.

Although there are many other compounds in development for different diseases, they are at earlier stages of development due mainly to the difficulty of delivering the oligonucleotides of choice to the target tissues. This is especially complicated in the case of siRNAs given their instability and ubiquitous nature of RNAses.

Given these difficulties, the compounds of the present invention which have improved stability against RNAses may be formulated in different ways, according to methods known in the art, to achieve an efficient delivery to the desired target tissue.

Therefore, a preferred embodiment of the present invention comprises the use of a compound according to the invention as a medicament. By way of example, a siRNA may be designed against the target mRNA of choice by methods known in the art. Then, this siRNA molecule is conjugated to the desired sphingolipid, and the resulting compound is administered to an individual, whose cell expression of the given target gene is to be silenced.

Also, a preferred embodiment of the present invention comprises a formulation or pharmaceutical composition which contains at least a compound as described in the preceding paragraphs.

Aspects of the invention also relate to a method of suppressing expression of a target gene in a cell, the method comprising contacting a cell with a compound comprising an oligonucleotide conjugated to a sphingolipid, as described. The oligonucleotide preferably comprises a nucleic acid sequence corresponding to a nucleic acid sequence of the target gene. The invention also provides a method of suppressing expression of a target gene in an organism, the method comprising administering such a compound to an organism. Also provided is a method of treating a disease in a mammal caused by aberrant expression of a target gene, the method comprising administering a compound as described to a mammal.

In another alternative embodiment of the present invention, a compound of the invention may be complexed with membrane disruptive agents and/or cationic lipids or a helper lipid molecule, and/or be included within a liposome.

A pharmaceutical formulation of the invention is in a form suitable for administration, e.g., systemic or local administration, into a cell or subject, including for example a human. Suitable forms, in part, depend upon the use or the route of entry, for example oral, transdermal, or by injection. Other factors are known in the art, and include considerations such as toxicity and forms that prevent the composition or formulation from exerting its effect.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art. For example, preservatives, stabilizers, dyes and flavouring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize.

Generally, an amount between 0.1 mg/kg and 100 mg/kg body weight/day of active ingredients is administered.

The formulations of the invention can be administered in unit dosage formulations containing conventional non-toxic pharmaceutically acceptable carriers, adjuvants and/or vehicles. Formulations can be in a form suitable for oral use, for example, as tablets, troches, lozenges, aqueous or oily suspensions, dispersible powders or granules, emulsion, hard or soft capsules, or syrups or elixirs. Compositions intended for oral use can be prepared according to any method known to the art for the manufacture of pharmaceutical compositions and such compositions can contain one or more such sweetening agents, flavouring agents, colouring agents or preservative agents in order to provide pharmaceutically elegant and palatable preparations. Tablets contain the active ingredient in admixture with non-toxic pharmaceutically acceptable excipients that are suitable for the manufacture of tablets.

These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more colouring agents, one or more flavouring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavouring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavouring and colouring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavouring agents.

Syrups and elixirs can be formulated with sweetening agents, for example glycerol, propylene glycol, sorbitol, glucose or sucrose. Such formulations can also contain a demulcent, a preservative, and flavouring and colouring agents. The pharmaceutical compositions can be in the form of a sterile injectable aqueous or oleaginous suspension.

This suspension can be formulated according to the known art using those suitable dispersing or wetting agents and suspending agents that have been mentioned above.

A sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The compounds of the invention can also be administered in the form of suppositories, e.g. for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

The compounds of the invention can be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

EXAMPLES

Given the common features of sphingolipids, as may be seen from FIG. 1, the following working examples of the present invention describe the conjugation of an oligonucleotide to sphingosine. However, they are considered to provide sufficient description for similar reactions to be performed with different sphingolipid molecules.

Due to the presence of the amino group in sphingosine it is possible to use the special reactivity of this amino group to form covalent bonds with oligonucleotides carrying electrophilic groups. This synthetic route is simple because there is no need to prepare a protected derivative of sphingosine but it requires the introduction of reactive groups in oligonucleotides. The following examples detail the use of amino, and carboxylic groups at the 5' and 3'-ends of oligonucleotides. The octathymidine sequence (T8: 5'-TTTTTTTT-3') was used as a model sequence for comparison purposes.

Synthesis of Oligonucleotide 5'-sphingosine Conjugates

Figure 2:
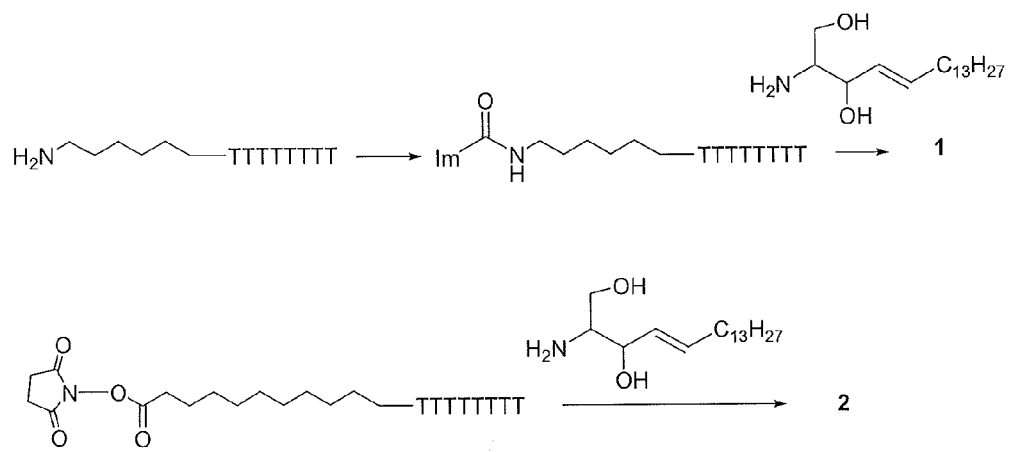
FIG. 2 shows a scheme of the reactions used for the preparation of oligonucleotides carrying sphingosine at the 5'-end.

The following reactions were tested (FIG. 2):
1) Reaction of sphingosine to 5'-amino-T8 by activation with carbonyldiimidazole. The amino group at the 5'-end of the oligonucleotide was introduced using 6-N-monomethoxytrityl-aminohexanol N,N-diisoproyl-O-cyanoethylphosphoramidite. The solid support carrying 5'-amino-T8 was reacted with a large excess of carbonyldiimidazole to generate a reactive carbonylimidazole function that was reacted with sphingosine. HPLC shows the formation of 22% of the desired oligonucleotide-5'-sphingosine conjugate (entry 1, Table in FIG. 5) that was isolated with a 10% yield (synthesis and purification).
2) Reaction of sphingosine to 5'-carboxy-$T_8$ oligonucleotide using 5'-carboxy modifier C10. The N-hydroxysuccinimide ester of the C10 activated carboxylic acid at 5'-end of the $T_8$ chain was synthesized using N-hydroxysuccinimidyl 10-oxa-decanoic acid 10-(N,N-diisoproyl-O-2'-cyanoethylphosphoramidite). The resulting CPG support was reacted with a solution of sphingosine in $CH_2Cl_2$ (10% triethylamine). HPLC analysis revealed the formation of the desired product in high conversion. After purification, the desired product (entry 2, Table in FIG. 5) was obtained in 20% yield. The final product was characterized by UV and mass spectrometry.
3) Introduction of sphingosine at 5' termini of siRNA, comprises various steps as described in the following paragraphs. Numerical references indicate corresponding chemical structures in FIG. 7.

Synthesis of $N^2$-tert-butoxycarbonyl (Boc)-sphingosine (2)

Sphingosine 1 (25 mg, 0.083 mmol) is dissolved in 1.5 mL of dichloromethane. Triethylamine (9.1 µL, 0.125 mmol) is added dropwise. Then, $Boc_2O$ (20 mg, 0.092 mmol) dissolved in 1 mL of dichloromethane is added. Reaction is stirred four hours at room temperature. Then, organic layer is extracted with dichloromethane and was washed with water (3×5 mL) and brine (3×5 mL). Finally, organic layer was dried on anhydrous $MgSO_4$. Solvent is removed to dryness and the resultant crude is used in the next step without further purification.

Synthesis of O-1,3-diacetyl-$N^2$-tert-butoxycarbonyl (Boc)-sphingosine (3) and O-1,3-diacetyl-sphingosine (4)

N-Boc sphingosine 2 (35 mg, 0.083 mmol) is dissolved in 3 mL of pyridine and then $Ac_2O$ (330 µL, 3.52 mmol) is carefully added. Reaction is stirred overnight at room temperature. The solvent is evaporated and the resultant crude is purified by flash chromatography ($CH_2Cl_2$ to $CH_2Cl_2$/MeOH 3%). Totally protected sphingosine 3 (36 mg, 0.074 mmol) is dissolved in a mixture of $CH_2Cl_2$/TFA 20%. Reaction is stirred 30 minutes at room temperature. Then, solvent is evaporated and crude is dissolved again in 3 mL of AcOEt and 0.5 mL of MeOH. Carbonate on polymer support (10.0 eq) was added and mixture was stirred for one hour at room temperature. Solid support was filtrated and solvent was evaporated to dryness yielding the resultant protected sphingosine 4 (27 mg, 0.070 mmol), which was used without further purification in the next step.

Conjugation with siRNA

The RNA sequence (X-GGCUACGUCCAG-GAGCGCAdTdT where X=an active ester and dT is a deoxythymidine nucleotide) (SEQ ID NO: 15) was prepared on a DNA synthesizer on 200 nmol scale. After the assembly of the RNA sequence a carboxyl group carrying a N-hydroxysuccinimide ester was introduced at the 5'-end using the corresponding phosphoramidite. At this point the solid support was treated with the protected sphingosine derivative 4 as follows: RNA support (200 nmol), 5 mg of compound 4 in 1 ml of 10% triethylamine in dichloromethane, 5 hours at room temperature. After the treatment, the solid support was washed with acetonitrile and treated with concentrated ammonia/ethanol (3/1, v/v). The ammonia solution was concentrated to dryness and treated with a solution of N-triethylamine tris(hydrofluoride) at 65° C. for 2.5 h. The RNAs were isolated by precipitation with ether and the resulting RNA was purified by reverse phase HPLC according to DMT off based protocols.

Synthesis of oligonucleotide 3'-sphingosine Conjugates

Figure 3:
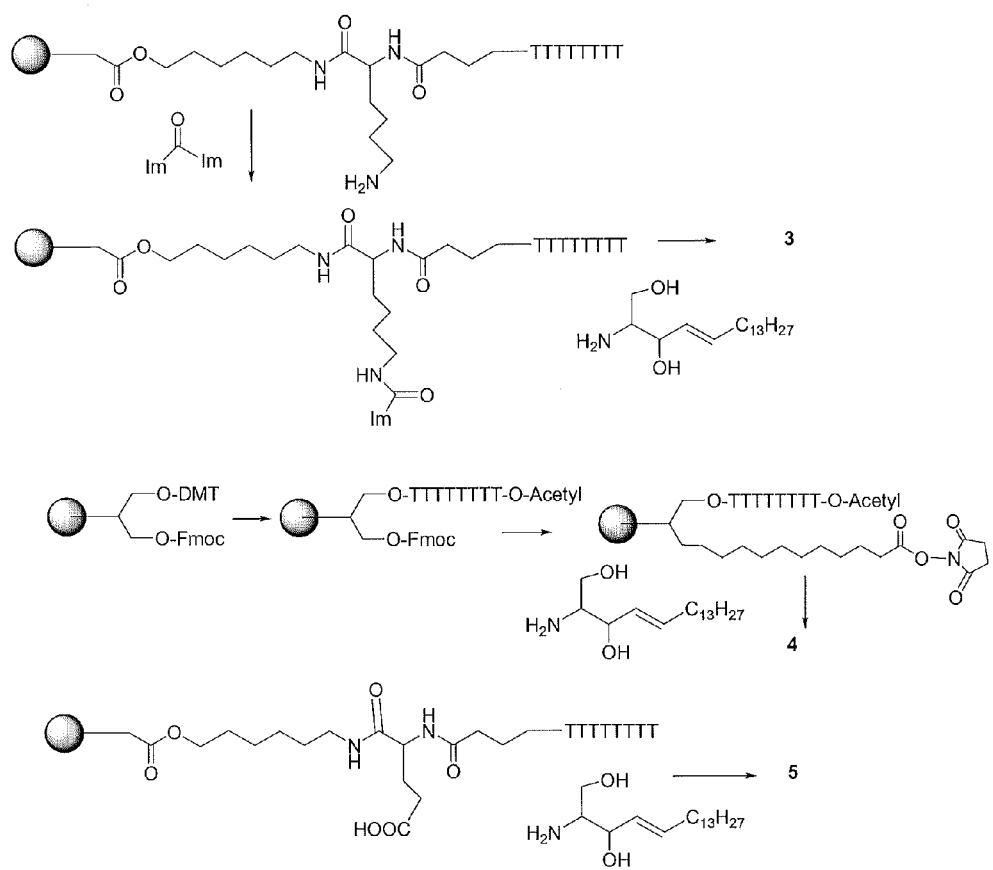
FIG. 3 shows a scheme of the reactions used for the preparation of oligonucleotides carrying sphingosine at the 3'-end.

The following reactions were tested (FIG. 3):
1) Reaction of sphingosine to T8-3'-amino by activation with carbonyldiimidazole. Octathymidine sequence (5'-TTTTTTTT-3'-amino) was assembled on controlled pore glass supports functionalized with lysine protected with the base labile group fluorenyloxycarbonyl (Fmoc) described by de la Torre et al 2002. After the assembly of the sequence, the solid support was treated with 0.1 M 1,8-diazabicyclo[5.4.0] undecene (DBU) to generate a free amino group. The solid support carrying T8-3'-amino was reacted with carbonyldiimidazole to generate a reactive carbonylimidazole function. The support was then treated with D-sphingosine (8.6 mg, 28 μmol) and the resulting support treated with concentrated ammonia. HPLC analysis revealed the formation of the desired product (entry 3, table in FIG. 5) that was obtained in 10% yield. The final product was characterized by UV and mass spectrometry.

2) Synthesis of 3'-sphingosine-octathymidine by introduction of an N-hydroxysuccinimide carboxy ester at the 3'-end using an asymmetric branched molecule followed by reaction with sphingosine. Octathymidine sequence (5'-TTTTTTTT-3') was assembled on controlled pore glass supports functionalized with an asymmetric branched molecule consisting of diol having one hydroxyl group protected with the acid labile group dimethoxytrityl and the other hydroxyl group protected with the base labile group fluorenylmethyloxycarbonyl (Fmoc) described by Aviñó et al 2004. After the assembly of the sequence, the solid support was acetylated with acetic anhydride and the resulting support was treated with 0.1 M 1,8-diazabicyclo[5.4.0]undecene (DBU). Then, the N-hydroxysuccinimide carboxy group at the 3'-end of the oligonucleotide was introduced using 10-oxadecanoic acid N-hydroxysuccinimide ester 10-(N,N-diisoproyl-O-cyanoethylphosphoramidite). The solid support carrying 3'-carboxy ester-T8 was reacted with D-sphingosine. The resulting support was treated with concentrated ammonia and the combined filtrates were analyzed by reverse phase HPLC. HPLC analysis revealed the formation of the desired product (entry 4, Table in FIG. 5) that was obtained in 4% yield. The final product was characterized by UV and mass spectrometry.

3) Reaction of sphingosine with 3'-carboxy-T8 by activation with dicyclohexylcarbodiimide and N-hydroxysuccinimide. Octathymidine sequence (5'-TTTTTTTT-3') was assembled on a controlled pore glass support functionalized with glutamic acid protected with the base labile group fluorenylmethyl (Fm) described by de la Torre et al. 2002. After the assembly of the sequence, the solid support was treated with 0.1 M DBU in acetonitrile. The solid support carrying 3'-carboxy-T8 was activated with dicyclohexylcarbodiimide and N-hydroxysuccinimide to generate an activated carboxyl function. The support was treated with D-sphingosine and the resulting support was treated with concentrated ammonia. The combined filtrates were analyzed by reverse phase HPLC. The desired compound (entry 5, Table in FIG. 5) eluted at 17 min.

4) Reaction of sphingosine with a 3'-amino-2'-O-methyl-RNA sequence by activation with carbonyldiimidazole.

Oligonucleotide sequence (5'-GGCUACGUCCAG-GAGCGCACCdTdT-3'-lysine) (SEQ ID NO:14) was assembled using the appropriate 2'-O-methyl-RNA and thymidine phosphoramidites. The resulting solid support was treated with DBU to generate a free amino group that was reacted with sphingosine as described previously. The resulting support was treated with concentrated ammonia for 1 hr at 55° C. and the filtrates were analyzed by reverse phase HPLC. HPLC analysis revealed the formation of the desired product that was obtained in 10% yield. The final product was characterized by UV and mass spectrometry.

Figure 4:
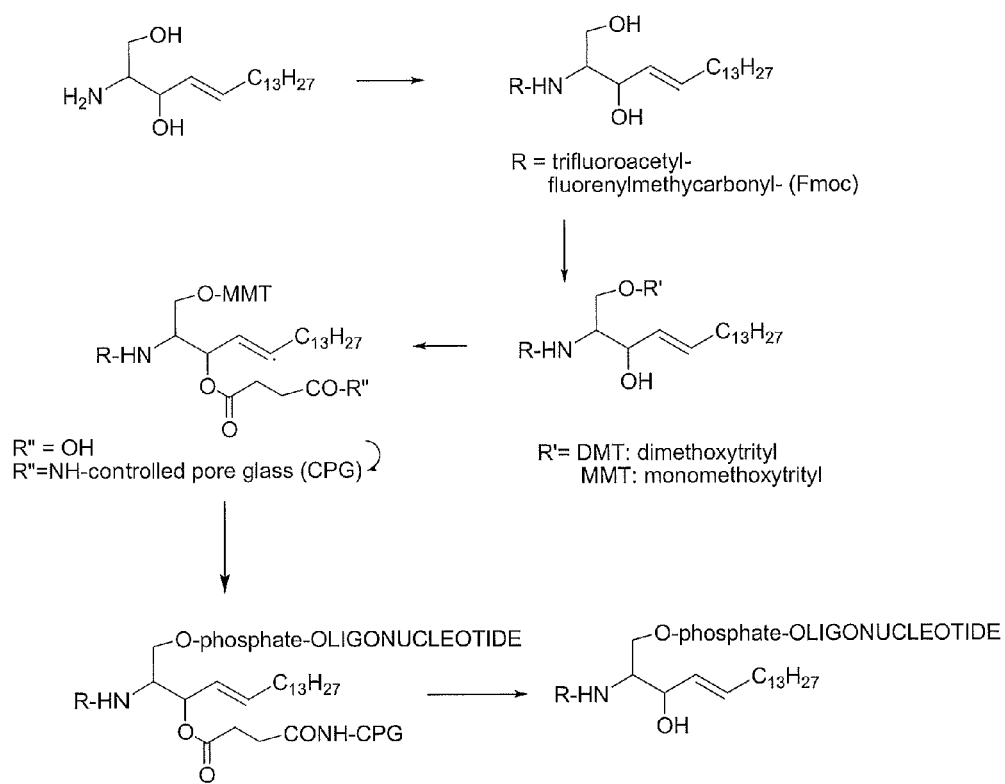
FIG. 4 shows a scheme of the preparation of a sphingosine derivative compatible with oligonucleotide synthesis.

Preparation of a Solid-Support Functionalized with Sphingosine for the Preparation of oligonucleotide 3'-sphingosine Conjugates (FIG. 4, Method A)

A protected derivative of sphingosine suitable for the incorporation on oligonucleotides using the phosphoramidite method was prepared. First the amino group of sphingosine was protected using the trifluoroacetyl and the fluorenylmethoxycarbonyl (Fmoc) groups. These two groups are labile to ammonia. Reaction of D-sphingosine with ethyl trifluoroacetate in dichloromethane yielded the desired trifluoroacetyl derivative of sphingosine in excellent yields (95% yield). Treatment of sphingosine with 9-fluorenylmethyl chloroformate and N,N-diisopropylethylamine in dichloromethane gave the desired Fmoc-protected derivative of sphingosine in 68% yield.

The second step was the protection of the primary hydroxyl of sphingosine with the acid labile dimethoxytrityl (DMT) group. Reaction of the trifluoroacetyl- and Fmoc-protected derivatives of sphingosine with dimethoxytrityl chloride in pyridine yielded the expected products as judged by TLC but the products were not stable on silica gel columns and for this reason these products were isolated in low yields. Then, the less labile monomethoxytrityl (MMT) group was selected. Reaction of the trifluoroacetyl-protected derivative of sphingosine with monomethoxytrityl chloride in pyridine yielded the expected product that could be isolated by silica gel in 63% yield.

Finally, the O-DMT and the O-MMT, N-trifluoroacetyl derivatives of sphingosine were reacted with succinic anhydride and dimethylaminopyridine to yield the corresponding hemisuccinates that were used for the functionalisation of amino-controlled pore glass (CPG) support. The resulting supports were used for the synthesis of oligonucleotides carrying sphingosine at the 3'-end. See FIG. 4 for explanatory diagram.

Synthesis of oligonucleotide 3'-sphingosine Conjugates

Oligonucleotide sequences (a: 5'-GGCUACGUCCAG-GAGCGCACCdTdT-sphingosine and b: 5'-GGCUACGUC-CAGGAGCGCACCdT$_{PS}$dT$_{PS}$-sphingosine, $_{PS}$: indicates the presence of a phosphorothioate linkage) were assembled on a CPG support functionalized with sphingosine protected with the base labile trifluoroacetyl group. The resulting supports were treated with a mixture of concentrated ammonia solution and ethanol (3/1, v/v). The filtered and dried products were treated with a solution of N-triethylamine tris(hydrofluoride) at 65° C. for 2.5 h. The RNAs were isolated by precipitation with ether and the resulting pellets were purified by reverse phase HPLC. The major peak was isolated on a 10% yield and had the expected mass. Sequence a: M found 7733, expected 7726; Sequence b: M found 7700, expected 7694, Sequence I: M found 7101, expected 7115; Sequence II: M found 7091, expected 7121; Sequence III: M found 7127, expected 7143; Sequence IV: M found 7092, expected 7111; Sequence V: M found 6630, expected 6626; Sequence VI: found 6457, expected 6457; Sequence VII: M+2Na$^+$ found 6146, expected 6102; Sequence A: M found 7033, expected 7029; Sequence B: M found 7036, expected 7035; Sequence C: M found 6542, expected 6540; Sequence D: M+2Na$^+$ found 6423, expected 6371; Sequence E: M+2Na$^+$ found 6060, expected 6016

Preparation of a Solid-Support Functionalized with Sphingosine for the Preparation of oligonucleotide 3'-sphingosine Conjugates (Method B)

Figure 6:
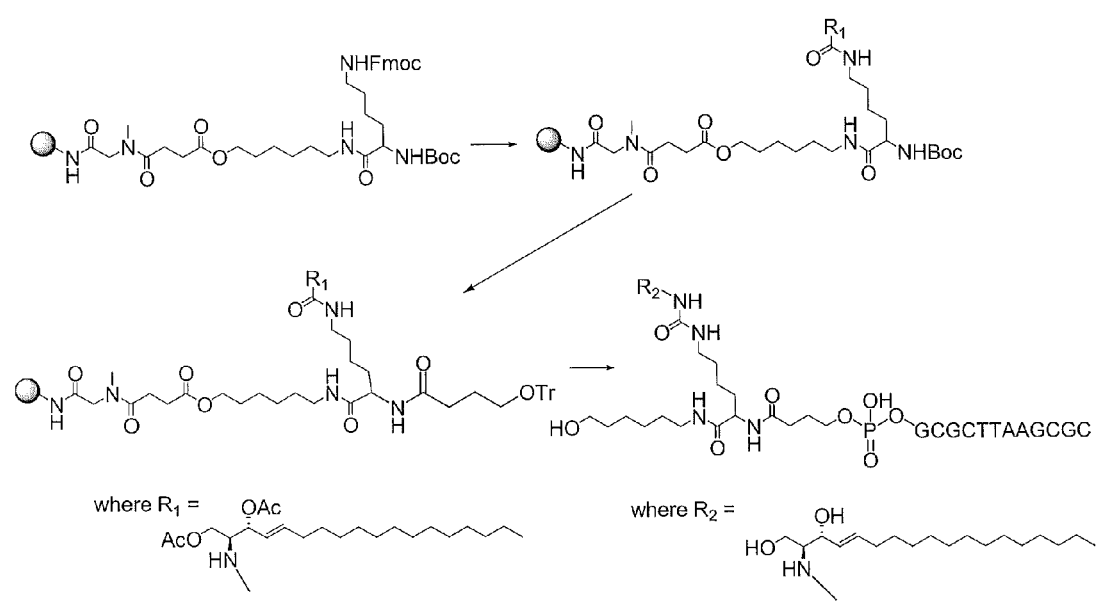
FIG. 6 shows a schematic representation of the synthesis of oligonucleotide 3'-sphingosine conjugates.

Alternatively a solid-support carrying sphingosine suitable for the preparation of 3'-sphingosine oligonucleotide conjugates was prepared as follows. First a diacetyl protected derivative of sphingosine was prepared from commercially available sphingosine. To this end, the amine group of sphingosine was protected with the Boc (tert-Butyloxycarbonyl) group using a mixture of Boc2O and triethylamine in dichloromethane at room temperature. Then, the resulting product was treated with acetic anhydride in pyridine to obtain the N-Boc-O, O-diacetyl-sphingosine derivative. Treatment of this compound with 20% trifluoroacetic acid in dichloromethane yielded the O,O-diacetyl protected derivative of sphingosine. This compound was reacted with a solid-support functionalized with Boc-Lys as described above but using p-nitrophenyl chloroformate instead of carbonyl diimidazole (FIG. 6).

In order to asses the use of this support for the synthesis of 3'-sphingosine oligonucleotide conjugates, an aliquot of this support was transferred to a DNA synthesizer and the following DNA sequence was assembled 5'-CGCGAATTCGCG-sphingosine-3' (SEQ ID NO: 13). Coupling yields ranged around 95%. The resulting solid support was treated with ammonia solution (32%), and desalted (Sephadex G-25). The expected 3'-sphingosine oligonucleotide conjugate was isolated, analyzed using analytical HPLC and confirmed by MALDI-TOF mass spectrometry (expected 4365, found 4352). See FIG. 6 for an explanatory diagram.

Study of the Biological Properties of RNA Duplexes Carrying 3'-sphingosine

Following the method of synthesis described in the previous section, 12 oligoribonucleotides were synthesised, nine of which contain sphingosine at their 3' end and three of which lack modifications. Of these oligonucleotides 7 correspond to an EGFP-silencing siRNA sense strand and 5 correspond to the corresponding antisense strand. The sequences and modifications are detailed below:

Sense Strand:

```
                                      SEQ ID NO: 1)
5'-GGCUACGUCCAGGAGCGCAdT*dT*-3'-sphingosine
Asterisks indicate phosphorothioate bonds,
and 3' sphingosine.

SEQ ID NO: 2)
5'-GGCUACGUCCAGGAGCGCAdTdT-3'-sphingosine
Contains sphingosine at 3'.

SEQ ID NO: 3)
5'-ggCUACGUCCAGGAGCGCAdT*dT*-3'-sphingosine
Asterisks indicate phosphorothioate bonds,
and both g at the 5' end are 2'-O-methyl
RNA, and sphingosine at 3'

SEQ ID NO: 4)
5'-ggCUACGUCCAGGAGCGCAdTdT-3'-sphingosine
Both g at the 5' end are 2'-O-methyl RNA,
and sphingosine at 3'.

SEQ ID NO: 5)
5'-GGCUACGUCCAGGAGCGCAdTdT-3'
No modifications

SEQ ID NO: 6)
5'-GGCUACGUCCAGGAGCGCA-3'-sphingosine
Contains sphingosine at 3' but no dT SEQ ID NO: 7)
5'-GGCUACGUCCAGGAGCGCA-3'
No modifications, no dT at the 3' end
```

Antisense strand:

```
                                      SEQ ID NO: 8)
5'-UGCGCUCCUGGACGUAGCCdT*dT*-3'-sphingosine
Asterisks indicate phosphorothioate bonds,
and 3' sphingosine.

SEQ ID NO: 9)
5'-UGCGCUCCUGGACGUAGCCdTdT-3'-sphingosine
Contains sphingosine at the 3' end.

SEQ ID NO: 10)
5'-UGCGCUCCUGGACGUAGCCdTdT-3'
No modifications

SEQ ID NO: 11)
5'-UGCGCUCCUGGACGUAGCC-3'-sphingosine
Contains sphingosine at 3' but no dT SEQ ID NO: 12)
5'-UGCGCUCCUGGACGUAGCC
No modifications, no dT at the 3' end
```

All these oligonucleotides were HPLC purified and characterised via mass spectrometry and analytical HPLC.

With the above described oligonucleotides 14 duplexes were prepared according to the following combinations:

Compound 1: 1-8, sphingosine and phosphorothioate on both strands
Compound 2: 1-10, sphingosine and phosphorothioate on the sense strand
Compound 3: 2-9, sphingosine on both strands
Compound 4: 2-10, sphingosine on the sense strand
Compound 5: 3-10, sphingosine, phosphorothioate and 2'-O-methylRNA on the sense strand
Compound 6: 4-8, sphingosine and 2'-O-methyl RNA on the sense strand, and sphingosine and phosphorothioate on the antisense strand
Compound 7: 4-10, sphingosine and 2'-O-methyl RNA on the sense strand, and no modifications on antisense strand
Compound 8: 5-8, no modifications on sense strand, and sphingosine and phosphorothioate on antisense
Compound 9: 5-9, no modifications on sense strand and sphingosine on antisense strand.
Compound 10: 5-10, no modifications on either strand.
Compound 11: 6-11, no protruding ends and sphingosine at 3' in both sense and antisense strands
Compound 12: 6-12, no protruding ends, sphingosine at 3' on the sense strand.
Compound 13: 7-11, no protruding ends, sphingosine at 3' on the antisense strand
Compound 14: 7-12, no protruding ends, no modifications All these compounds are formed by hybridisation of indicated sense and antisense strands in such a way that the resulting siRNA has a double-stranded region of 19 nucleotides, and, for Compounds 1 to 10 dinucleotide overhangs at 3', whereby these overhanging nucleotides are deoxy-thymidine.

The 14 compounds were then analysed for their gene-silencing capacity in vitro cell cultures, and also for their stability in serum.

Stability in Biological Fluids: Mouse Serum

Stock solutions of the above compounds were prepared in PBS (phosphate buffered saline) at a concentration of 200 µM. Then, 5 µl of each of these stock solutions was added to 45 µl of a solution containing 10% mouse serum diluted in PBS.

The resulting solution was incubated at 37° C. for 30 minutes or for 24 hours, after which the solutions were analysed for remaining intact compound using HPLC-UV.

The following table shows the amount of intact compound recovered after the indicated incubation time for each of the compounds analysed.

| COMPOUND | 30 minutes | 24 hours |
|---|---|---|
| 1 | 74 | 0 |
| 2 | 66 | 68 |
| 3 | 100 | 48 |
| 4 | 84 | 11 |
| 5 | 74 | 78 |
| 6 | 71 | 0 |
| 7 | 81 | 10 |
| 8 | 69 | 68 |
| 9 | 48 | 21 |
| 10 | 0 | 0 |

As may be seen, the control unmodified siRNA (compound 10) was completely degraded after only 30 minutes in contact with mouse serum, whereas the different sphingosine conjugated molecules clearly showed enhanced stability against RNAses.

In Vitro Gene Silencing: MDCK-EGFP Cells

As a model to test effectiveness of the above described siRNA conjugates with sphingosine targeting EGFP, a MDCK-EGFP cell line, a modification of the original MDCK cell line stably transfected with a GFP expression vector was employed. MDCK-EGFP cells were transfected with 100 nM of different compounds and Lipofectamine 2000 as a transfectant agent. All transfections were done following standard manufacturer's conditions. Ten different modified siRNAs were tested, described as Compounds 1 to 10, in preceding paragraphs. In the same transfection two different siRNAs were used as controls, a naked siRNA with the same EGFP sequence and a scramble siRNA. For each condition fluorescence pictures were taken at 24, 48, 72 and 96 hours to evaluate possible variations in the levels of fluorescent protein. Cell pellets were then collected and processed by realtime PCR. In order to quantify the results obtained by realtime RT-PCR, we used the Comparative Threshold Method.

Figure 8:
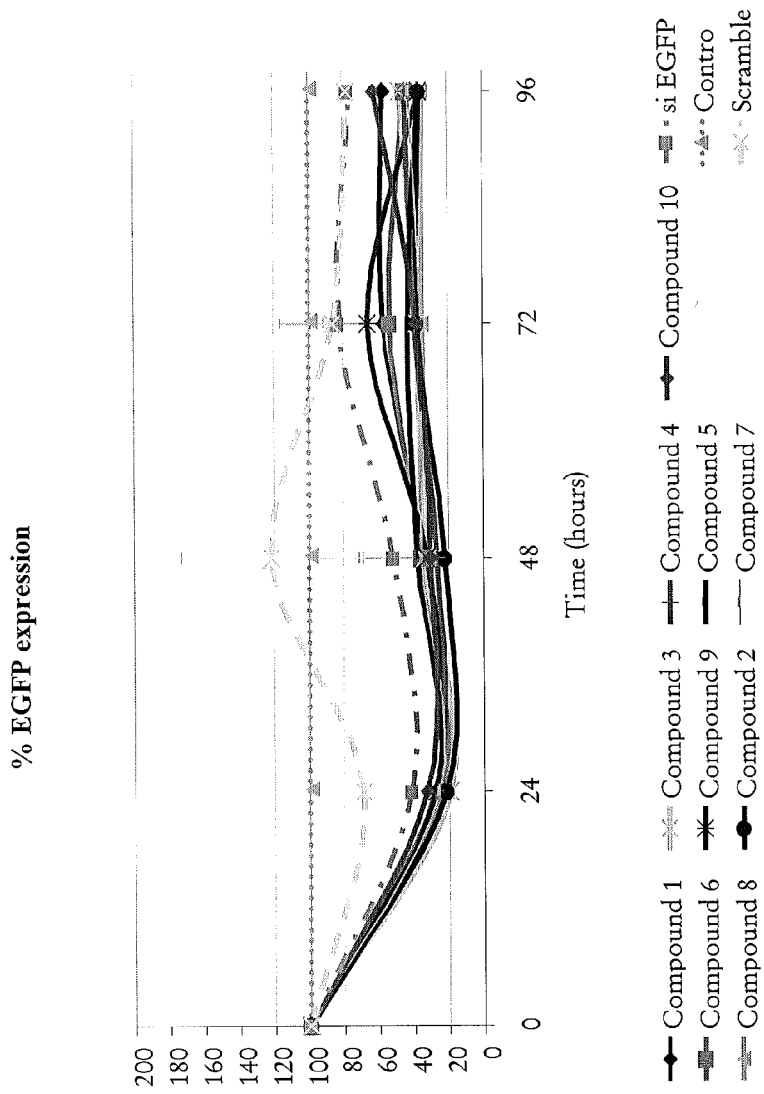
FIGS. 8 and 9 show EGFP temporal expression in MDCK-EGFP cells after transfection of different EGFP-specific siRNA molecules of the invention, measured by RT-PCR, as described in the working examples. Y axis indicates the percentage of EGFP expression with respect to control (which is considered to be 100%), and X axis represents time lapsed in hours from the moment of transfection (time=0) to a maximum of 96 hours.

As results show (FIG. 8), not only the mechanism of action of siRNA is unaffected when sphingosine modifications are added to the siRNA structure but an increase in its interference effectiveness is achieved in the longer time points regarding the EGFP naked sequence. At 96 hours a total recovery of EGFP mRNA levels is not observed when using the compounds of the invention, whereas a complete recovery of EGFP expression levels occurred at this time-point when naked siRNAs were transfected.

Figure 9:
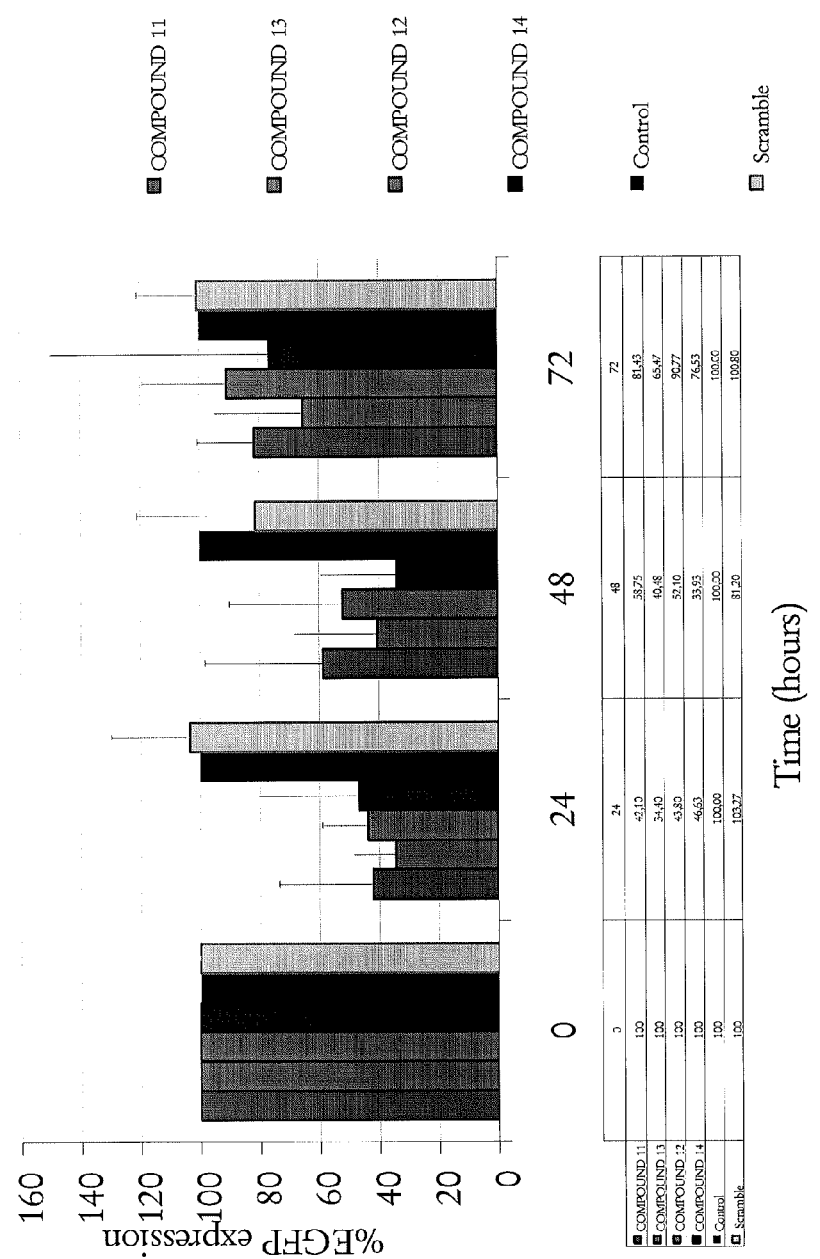

Furthermore, siRNA compounds with a 19 nucleotide blunt-ended structure modified with sphingosine were also analysed for gene silencing efficiency. As may be seen from FIG. 9, compounds 11 to 13 (described in preceding paragraphs) containing sphingosine at different positions have a similar RNA interfering efficiency to compound 14 (which has no sphingosine attached).

From these results, one may derive that the conjugation of sphingosine to the basic structure of siRNAs improves stability of said siRNA molecule without affecting its efficacy, and even improving it.

Figure 10:
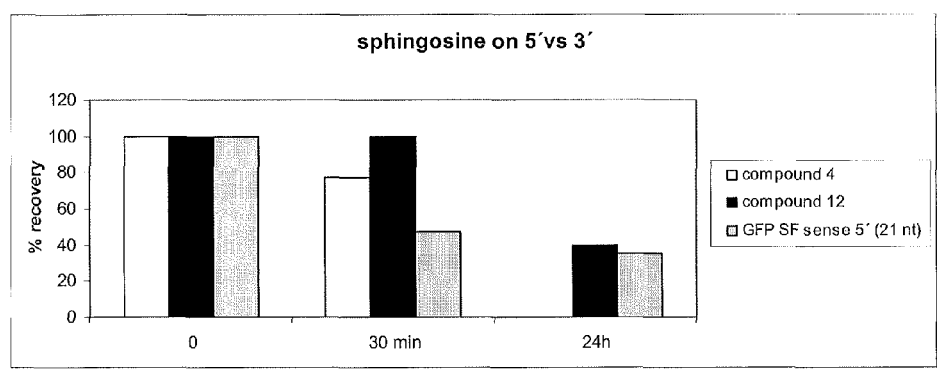
FIG. 10, shows a comparison of compound stability in serum of siRNA molecules conjugated to sphingosine on their 3' or 5' end.

Furthermore, siRNAs were also conjugated to sphingosine on their 5' end. FIG. 10 shows a comparison between compounds having 21 nt structures with overhangs, 19 nucleotide blunt-ended structures, with sphingosine on 3' or on 5' ends of their sense strands. As may be derived, all these structures resulted in enhanced resistance to degradation in serum compared to unconjugated siRNAs.

As is clearly derived from the above working examples of the present invention, conjugation of RNA interfering structures with sphingosine, is a highly relevant contribution to the field, as it increases the compounds' stability in serum, a major hurdle for delivery of these compounds to the desired target tissues, whilst maintaining a good gene-silencing capacity.

REFERENCES

Aviñó, A., Grimau, M. G., et al. (2004) "Synthesis and triple-helix stabilization properties of branched oligonucleotides carrying 8-aminoadenine." Helv. Chim. Acta, 87:303-316.

Boutorine, A. S. Kostina, E. V. (1993). "Reversible covalent attachment of cholesterol to oligodeoxyribonucleotides for studies of the mechanisms of their penetration into eukaryotic cells". Biochemie, 75:35-41.

Cerutti, L., N. Mian, et al. (2000). "Domains in gene silencing and cell differentiation proteins: the novel PAZ domain and redefinition of the Piwi domain." Trends Biochem Sci 25(10): 481-2.

Collins, R. E. and X. Cheng (2005). "Structural domains in RNAi." FEBS Lett 579(26): 5841-9.

De la Torre, B. G., Morales, J. C., et al. (2002) "Synthesis of oligonucleotides carrying anchoring groups and their use in the preparation of oligonucleotide-gold conjugates." Helv. Chim. Acta, 85:2594-2607.

Elbashir, S. M., W. Lendeckel, et al. (2001). "RNA interference is mediated by 21- and 22-nucleotide RNAs." Genes Dev 15(2): 188-200.

Fire, A., S. Xu, et al. (1998). "Potent and specific genetic interference by double-stranded RNA in Caenorhabditis elegans." Nature 391(6669): 806-11.

Godard, G., Boutorine, A. S., et al. (1995). "Antisense effects of cholesterol-oligodeoxynucleotide conjugates associated with poly(alkylcyanoacrylate) nanoparticles. Eur. J. Biochem., 232:404-410.

Gryaznov, S. M., Lloyd, D. H. (1993). "Modulation of oligonucleotide duplex and triplex stability via hydrophobic interactions" Nucleic Acids Res., 21:5909-5915.

Hutvagner, G. and P. D. Zamore (2002). "A microRNA in a multiple-turnover RNAi enzyme complex." Science 297 (5589): 2056-60.

LeDoan, T., Etore, F., et al. (1999). "Cell binding, uptake and cytosolic partition of HIV anti-gag phosphodiester oligonucleotides 3'-linked to cholesterol derivatives in macrophages" Bioorg. Med. Chem., 7:2263-2269.

Liu, J., M. A. Carmell, et al. (2004). "Argonaute2 is the catalytic engine of mammalian RNAi." Science 305(5689): 1437-41.

Ma, J. B., Y. R. Yuan, et al. (2005). "Structural basis for 5'-end-specific recognition of guide RNA by the A. fulgidus Piwi protein." Nature 434(7033): 666-70.

Nykanen, A., B. Haley, et al. (2001). "ATP requirements and small interfering RNA structure in the RNA interference pathway." Cell 107(3): 309-21.

Orban, T. I. and E. Izaurralde (2005). "Decay of mRNAs targeted by RISC requires XRN1, the Ski complex, and the exosome." Rna 11(4): 459-69.

Parrish, S., J. Fleenor, et al. (2000). "Functional anatomy of a dsRNA trigger: differential requirement for the two trigger strands in RNA interference." Mol Cell 6(5): 1077-87.

Rand, T. A., S. Petersen, et al. (2005). "Argonaute2 cleaves the anti-guide strand of siRNA during RISC activation." Cell 123(4): 621-9.

Song, J. J., S. K. Smith, et al. (2004). "Crystal structure of Argonaute and its implications for RISC slicer activity." *Science* 305(5689): 1434-7.

Soutschek, J., A. Akinc, et al. (2004). "Therapeutic silencing of an endogenous gene by systemic administration of modified siRNAs." *Nature* 432(7014): 173-8.

Wolfrum C., Shi, S., Jayaprakash, et al. (2007). "Mechanism and optimization of in vivo delivery of lipophillic siRNAs" *Nature Biotech.* 25: 1149-1157.

Zelphati, O., Wagner, E., et al. (1994). "Synthesis and anti-HIV activity of thiocholesteryl-coupled phosphodiester antisense oligonucleotides incorporated into immunoliposomes" *Antiviral Res.*, 25:13-25.

The invention claimed is:

1. A process for the preparation of an oligonucleotide-sphingosine conjugate consisting, of an oligonucleotide conjugated to a sphingosine molecule, the process comprising conjugating an oligonucleotide to the sphingosine molecule, thereby producing the oligonucleotide-sphingosine conjugate.

2. The process according to claim 1, wherein the sphingosine molecule is provided on a solid support, and conjugation to the oligonucleotide takes place on said solid support, and wherein (a) the assembly of the oligonucleotide sequence takes place on the solid support, (b) the assembly of the oligonucleotide sequences takes place from an alcohol function of the sphingosine molecule by successive additions of the nucleoside phosphoramidites, or (c) the sphingosine molecule is reacted with an activated oligonucleotide in solution.

3. The process according to claim 1, wherein the sphingosine molecule is conjugated to the oligonucleotide by phosphate or amide bonds.

4. The process according to claim 1 or claim 3, comprising the steps of:
    binding an amine or carboxy group to at least one terminus of the oligonucleotide;
    activating the amino or carboxy group; and
    allowing an amino group on the sphingosine molecule to attack the activated group on the oligonucleotide, such that the activated group is displaced and the oligonucleotide-sphingosine conjugate is formed.

5. A process for producing an oligonucleotide-sphingosine conjugate in which an oligonucleotide is conjugated to a sphingosine molecule, the process comprising the steps of:
    binding an amine or carboxy group to at least one terminus of the oligonucleotide;
    activating the amino or carboxy group; and
    allowing an amino group on the sphingosine molecule to attack the activated group on the oligonucleotide, such that the activated group is displaced and the oligonucleotide-sphingosine conjugate is produced.

6. The process according to claim 5, wherein the sphingosine molecule is conjugated to the oligonucleotide by phosphate or amide bonds.

7. The process according to any one of claims 1, 3, or 5, wherein the oligonucleotide comprises structurally modified nucleotides.

8. The process according to claim 7, wherein the structurally modified nucleotides are selected from 2'-O-methyl nucleotides, 2'-amino nucleotides, nucleotides containing 2'-O methylene bridges, nucleotides containing 4'-C methylene bridges, or phosphorothioate-modified nucleotides.

9. The process according to any one of claim 1, 3, or 5, wherein the oligonucleotide comprises alternative bases selected from inosine, 4-thiouracil, 5-bromouracil, 5-iodouracil, or 3-(aminoallyl)uracil.

10. A compound consisting of an oligonucleotide-sphingosine conjugate in which the oligonucleotide is conjugated to a sphingosine molecule.

11. The compound according to claim 10, wherein the sphingosine molecule is D-sphingosine.

12. The compound according to claim 10, wherein the sphingosine molecule is conjugated to the 3' end of the oligonucleotide, to the 5' end of the oligonucleotide, or to each of the 3' and 5' ends of the oligonucleotide.

13. The compound according to claim 10, wherein the oligonucleotide comprises deoxyribonucleotides, ribonucleotides, or both.

14. The compound according to claim 10, which is hybridized by base complementarity to a complementary oligonucleotide.

15. The compound according to claim 14, wherein the hybridized oligonucleotides an siRNA.

16. The compound according to claim 14, wherein the sphingosine molecule is conjugated to any of the following:
    the sense strand, or
    the antisense strand, or
    both the sense and antisense strands of the hybridized oligonucleotide.

17. The compound according to claim 14, wherein the sphingosine molecule is conjugated to the 3' end of the oligonucleotide, to the 5' end of the oligonucleotide, or to each of the 3' and 5' ends of the oligonucleotide.

18. The compound according to claim 14, wherein the oligonucleotide is between 15 and 25 nucleotides in length.

19. The compound according to claim 14, wherein the hybridized oligonucleotide comprises a 19 nucleotide double stranded region with a dinucleotide overhang at the 3' end.

20. The compound according to claim 19, wherein the hybridized oligonucleotide comprises a 19 nucleotide double stranded region with a dinucleotide overhang at the 3' end, wherein the dinucleotide is dTdT.

21. The compound according to claim 14, wherein the hybridized oligonucleotide comprises a 19 nucleotide double stranded structure with blunt ends.

22. The compound according to claim 14, wherein the hybridized oligonucleotide comprises a 19 nucleotide double stranded structure with between 1 and 3 overhanging nucleotides at the 3' end.

23. The compound according to claim 10, wherein the oligonucleotide of the compound is provided as naked RNA.

24. The compound according to claim 10, wherein the oligonucleotide comprises structurally modified nucleotides.

25. The compound according to claim 24, wherein the structurally modified nucleotides are selected from 2'-O-methyl nucleotides, 2'-amino nucleotides, nucleotides containing 2'-O methylene bridges, nucleotides containing 4'-C methylene bridges, or phosphorothioate-modified nucleotides.

26. The compound according to claim 10, wherein the oligonucleotide comprises alternative bases selected from inosine, 4-thiouracil, 5-bromouracil, 5-iodouracil, or 3-(aminoallyl)uracil.

27. A pharmaceutical composition comprising the compound according to claim 10 and a pharmaceutically acceptable carrier or diluent.

28. A method of suppressing expression of a target gene in a cell, the method comprising contacting the cell with the compound according to claim 10, wherein the nucleic acid sequence of the oligonucleotide of the compound corresponds to a nucleic acid sequence of the target gene.

29. A method of suppressing expression of a target gene in an organism, the method comprising administering the compound according to claim 10 to the organism, wherein the nucleic acid sequence of the oligonucleotide of the compound corresponds to a nucleic acid sequence of the target gene.

30. A method of treating a disease in a mammal caused by aberrant expression of a target gene, the method comprising administering the compound according to claim 10 to the mammal, wherein the nucleic acid sequence of the oligonucleotide of the compound corresponds to a nucleic acid sequence of the target gene.

* * * * *

SEQUENCE LISTING

```
<160> NUMBER OF SEQ ID NOS: 15

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      3'-sphingosine conjugate oligonucleotide
<220> FEATURE:
<223> OTHER INFORMATION: Description of Combined DNA/RNA Molecule:
      Synthetic 3'-sphingosine conjugate oligonucleotide
<220> FEATURE:
<221> NAME/KEY: modified_base
<222> LOCATION: (20)..(21)
<223> OTHER INFORMATION: Deoxythymidine
<220> FEATURE:
<221> NAME/KEY: misc_feature
<222> LOCATION: (20)..(21)
<223> OTHER INFORMATION: Phosphorothioate bond
<220> FEATURE:
<223> OTHER INFORMATION: 3' sphingosine

<400> SEQUENCE: 1
ggcuacgucc aggagcgcat t                                             21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      3'-sphingosine conjugate oligonucleotide
<220> FEATURE:
<223> OTHER INFORMATION: Description of Combined DNA/RNA Molecule:
      Synthetic 3'-sphingosine conjugate oligonucleotide
<220> FEATURE:
<221> NAME/KEY: modified_base
<222> LOCATION: (20)..(21)
<223> OTHER INFORMATION: Deoxythymidine
<220> FEATURE:
<223> OTHER INFORMATION: 3' sphingosine

<400> SEQUENCE: 2
ggcuacgucc aggagcgcat t                                             21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      3'-sphingosine conjugate oligonucleotide
<220> FEATURE:
<223> OTHER INFORMATION: Description of Combined DNA/RNA Molecule:
      Synthetic 3'-sphingosine conjugate oligonucleotide
<220> FEATURE:
<221> NAME/KEY: modified_base
<222> LOCATION: (1)..(2)
<223> OTHER INFORMATION: 2'-O-methylguanosine
<220> FEATURE:
<221> NAME/KEY: modified_base
<222> LOCATION: (20)..(21)
```

```
<223> OTHER INFORMATION: Deoxythymidine
<220> FEATURE:
<221> NAME/KEY: misc_feature
<222> LOCATION: (20)..(21)
<223> OTHER INFORMATION: Phosphorothioate bond
<220> FEATURE:
<223> OTHER INFORMATION: 3' sphingosine

<400> SEQUENCE: 3
ggcuacgucc aggagcgcat t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      3'-sphingosine conjugate oligonucleotide
<220> FEATURE:
<223> OTHER INFORMATION: Description of Combined DNA/RNA Molecule:
      Synthetic 3'-sphingosine conjugate oligonucleotide
<220> FEATURE:
<221> NAME/KEY: modified_base
<222> LOCATION: (1)..(2)
<223> OTHER INFORMATION: 2'-O-methylguanosine
<220> FEATURE:
<221> NAME/KEY: modified_base
<222> LOCATION: (20)..(21)
<223> OTHER INFORMATION: Deoxythymidine
<220> FEATURE:
<223> OTHER INFORMATION: 3' sphingosine

<400> SEQUENCE: 4
ggcuacgucc aggagcgcat t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      unmodified oligonucleotide
<220> FEATURE:
<223> OTHER INFORMATION: Description of Combined DNA/RNA Molecule:
      Synthetic unmodified oligonucleotide
<220> FEATURE:
<221> NAME/KEY: modified_base
<222> LOCATION: (20)..(21)
<223> OTHER INFORMATION: Deoxythymidine

<400> SEQUENCE: 5
ggcuacgucc aggagcgcat t                                              21

<210> SEQ ID NO 6
<211> LENGTH: 19
<212> TYPE: RNA
<213> ORGANISM: Artificial Sequence
<220> FEATURE:
<223> OTHER INFORMATION: Description of Artificial Sequence: Synthetic
      3'-sphingosine conjugate oligonucleotide
<220> FEATURE:
<223> OTHER INFORMATION: 3' sphingosine

<400> SEQUENCE: 6
ggcuacgucc aggagcgca                                                 19

<210> SEQ ID NO 7
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
    unmodified oligonucleotide

<400> SEQUENCE: 7
ggcuacgucc aggagcgca                                                  19

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      3'-sphingosine conjugate oligonucleotide
<220> FEATURE:
<223> OTHER INFORMATION: Description of Combined DNA/RNA Molecule:
      Synthetic 3'-sphingosine conjugate oligonucleotide
<220> FEATURE:
<221> NAME/KEY: modified_base
<222> LOCATION: (20)..(21)
<223> OTHER INFORMATION: Deoxythymidine
<220> FEATURE:
<221> NAME/KEY: misc_feature
<222> LOCATION: (20)..(21)
<223> OTHER INFORMATION: Phosphorothioate bond
<220> FEATURE:
<223> OTHER INFORMATION: 3' sphingosine

<400> SEQUENCE: 8
ugcgcuccug gacguagcct t                                               21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      3'-sphingosine conjugate oligonucleotide
<220> FEATURE:
<223> OTHER INFORMATION: Description of Combined DNA/RNA Molecule:
      Synthetic 3'-sphingosine conjugate oligonucleotide
<220> FEATURE:
<221> NAME/KEY: modified_base
<222> LOCATION: (20)..(21)
<223> OTHER INFORMATION: Deoxythymidine
<220> FEATURE:
<223> OTHER INFORMATION: 3' sphingosine

<400> SEQUENCE: 9
ugcgcuccug gacguagcct t                                               21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      unmodified oligonucleotide
<220> FEATURE:
<223> OTHER INFORMATION: Description of Combined DNA/RNA Molecule:
      Synthetic unmodified oligonucleotide
<220> FEATURE:
<221> NAME/KEY: modified_base
<222> LOCATION: (20)..(21)
<223> OTHER INFORMATION: Deoxythymidine

<400> SEQUENCE: 10
ugcgcuccug gacguagcct t                                               21

<210> SEQ ID NO 11
<211> LENGTH: 19
<212> TYPE: RNA
<213> ORGANISM: Artificial Sequence
<220> FEATURE:
```

```
<223> OTHER INFORMATION: Description of Artificial Sequence: Synthetic
      3'-sphingosine conjugate oligonucleotide
<220> FEATURE:
<223> OTHER INFORMATION: 3' sphingosine

<400> SEQUENCE: 11
ugcgcuccug gacguagcc                                              19

<210> SEQ ID NO 12
<211> LENGTH: 19
<212> TYPE: RNA
<213> ORGANISM: Artificial Sequence
<220> FEATURE:
<223> OTHER INFORMATION: Description of Artificial Sequence: Synthetic
      unmodified oligonucleotide

<400> SEQUENCE: 12
ugcgcuccug gacguagcc                                              19

<210> SEQ ID NO 13
<211> LENGTH: 12
<212> TYPE: DNA
<213> ORGANISM: Artificial Sequence
<220> FEATURE:
<223> OTHER INFORMATION: Description of Artificial Sequence: Synthetic
      3'-sphingosine conjugate oligonucleotide
<220> FEATURE:
<223> OTHER INFORMATION: 3' sphingosine

<400> SEQUENCE: 13
cgcgaattcg cg                                                     12

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      unmodified oligonucleotide
<220> FEATURE:
<223> OTHER INFORMATION: Description of Combined DNA/RNA Molecule:
      Synthetic unmodified oligonucleotide
<220> FEATURE:
<221> NAME/KEY: modified_base
<222> LOCATION: (22)..(23)
<223> OTHER INFORMATION: Deoxythymidine

<400> SEQUENCE: 14
ggcuacgucc aggagcgcac ctt                                         23

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      starting DNA/RNA sequence
<220> FEATURE:
<223> OTHER INFORMATION: Description of Combined DNA/RNA Molecule:
      Synthetic starting DNA/RNA sequence
<220> FEATURE:
<223> OTHER INFORMATION: 5' active ester
<220> FEATURE:
<221> NAME/KEY: modified_base
<222> LOCATION: (20)..(21)
<223> OTHER INFORMATION: Deoxythymidine

<400> SEQUENCE: 15
ggcuacgucc aggagcgcat t                                           21
```